United States Patent [19]

Merger et al.

[11] Patent Number: 4,777,265

[45] Date of Patent: Oct. 11, 1988

[54] PREPARATION OF ACRYLATES AND METHACRYLATES

[75] Inventors: Franz Merger, Frankenthal; Hans-Martin Hutmacher, Ludwigshafen; Wolfgang Schwarz, Pfintzal; Gerhard Nestler, Ludwigshafen; Maria G. Szucsanyi, Ludwigshafen; Rudolf Mueller-Mall, Neuhofen, all of Fed. Rep. of Germany

[73] Assignee: BASF Aktiengesellschaft, Ludwigshafen, Fed. Rep. of Germany

[21] Appl. No.: 22,110

[22] Filed: Mar. 5, 1987

[30] Foreign Application Priority Data

Mar. 11, 1986 [DE] Fed. Rep. of Germany ....... 3607995

[51] Int. Cl.$^4$ .......................................... C07D 233/32
[52] U.S. Cl. ................................... 548/320; 540/460; 540/492; 544/318
[58] Field of Search ..................... 548/320; 544/318; 540/460, 492

[56] References Cited

U.S. PATENT DOCUMENTS 2,871,223  1/1959  Hankins et al. ................. 548/320
3,989,707  11/1976 Janssen et al. ................. 546/199
4,211,804  7/1980  Brizzolara ..................... 427/377

FOREIGN PATENT DOCUMENTS 2527261  1/1986  Fed. Rep. of Germany ...... 546/199

OTHER PUBLICATIONS

Chemical Abstracts, 90:105789a (1979) [Span. 464, 639, 9/1/78].
Chemical Abstracts, 95:169841x (1981) [Sivaram, S., et al., Polym. Bull. 1981, 5, 159–66].
Chemical Abstracts, 102:20483m (1985) [Ger. Offen. 3,324,917, 1/17/85].
Chemical Abstracts, 104:6318x (1986) [Japan Kokai 60, 147,430, 8/3/85].
Chemical Abstracts, 106:6694h (1987) [Mikestik, A., et al., 25(5–6), 147–158].
Chemical Abstracts, vol. 102, No. 5, Feb. 4, 1985, Abstract Number 102 :45947e.
Chemical Abstracts, vol. 81, No. 14, Oct. 7, 1974, Abstract Number 81: 78465x.

Primary Examiner—Richard A. Schwartz
Attorney, Agent, or Firm—Keil & Weinkauf

[57] ABSTRACT

Acrylates or methacrylates I

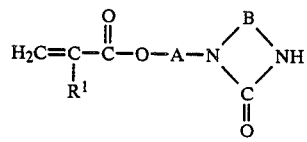

(A and B=$C_2$–$C_5$-alkylene, $R^1$=H, $CH_3$) are prepared by reacting an acrylate or methacrylate II

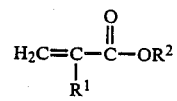

($R^2$=$C_1$–$C_4$-alkyl) with a heterocycle III

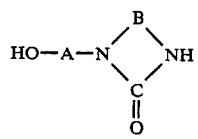

in the presence of titanium alcoholates chelate compounds of the metals titanium, zirconium, iron and zinc with 1,3-dicarbonyl compounds.

7 Claims, No Drawings

PREPARATION OF ACRYLATES AND METHACRYLATES

The present invention relates to a novel, improved process for preparing an acrylate or methacrylate of the formula I

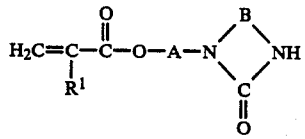   I where $R^1$ is hydrogen or methyl and A and B are each branched or unbranched alkylene of 2 to 5 carbon atoms.

These compounds are interesting comonomers, for example for preparing paint dispersions or leather assistants (eg. U.S. Pat. Nos. 2,828,224 or 3,356,627). They are obtained, for example as described in U.S. Pat. No. 2,871,223, by transesterifying acryloyl or methacryloyl chloride with an imidazolidin-2-one derivative in the presence of a tertiary amine or pyridine. However, this reaction gives rise to stoichiometric amounts of ammonium chlorides or pyridinium hydrochloride, which need to be separated off before the products are used. As a result, the process is technically complicated and virtually unsuitable for industrial production. Considerable amounts of double-substituted byproducts are also formed.

It is an object of the present invention to provide an industrially feasible simple and selective process for preparing I in sufficient purity for use without costly cleaning operations as components for dispersions.

We have found that this object is achieved with a process whereby an acrylate or methacrylate of the formula I

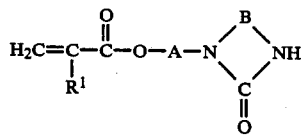   I where $R^1$ is hydrogen or methyl and A and B are each branched or unbranched alkylene of 2 to 5 carbon atoms is advantageously prepared by reacting an acrylate or methacrylate of the formula II

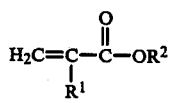   II where $R^2$ is an alkyl of 1 to 4 carbon atoms with a heterocycle of the formula III

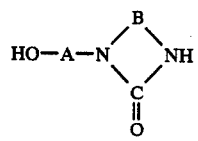   III in the presence of a titanium alcoholate or of a chelate compound of one of the metals titanium, zirconium, iron or zinc with a 1,3-dicarbonyl compound.

The success of the process is surprising, since it was to be expected that the bifunctional character of I would easily give rise to secondary reactions with II which would prevent the direct use of I for dispersions. An expected secondary or competing reaction with respect to the reaction according to the invention was in particular base-catalysed Michael addition. This addition of an acrylate or methacrylate onto a urea derivative, for example the diisocyanate used in U.S. Pat. No. 4,211,804, onto a benzimidazolone derivative as described in German Laid-Open Application DOS No. 2,527,261 (claim 10c and Example 25) and German published application DAS No. 1,545,997, or onto a pyrimidine derivative (see for example Tetrahedron Letters No. 53, 4605–4606) is generally known. For example, in the transesterification of methacrylates with 1-(2-hydroxyethyl)imidazolidin-2-one, the resulting 1-(2-methacryloyloxyethyl)imidazolidin-2-ones can easily undergo secondary reactions to form 1-(2-methacryloyloxyethyl)-3-(2-carbalkoxypropyl)imidazolidin-2-ones (Michael products) and/or 1-(2-methacryloyloxyethyl)-3-methacroylimidazolidin-2-one. These secondary reactions are observed for example if the transesterification is carried out in the presence of widely used catalysts such as sodium methylate, potassium carbonate, potassium hydroxide or 1,8-diazabicyclo[5.4.0]undec-7-ene (DBU) (see Comparative Example 6). Separation is not possible on an industrial scale, owing to the thermolability and polymerization tendency of the product.

On using methyl methacrylate and 1-(2-hydroxyethyl)imidazolidin-2-one, the reaction can be represented by the following equation:

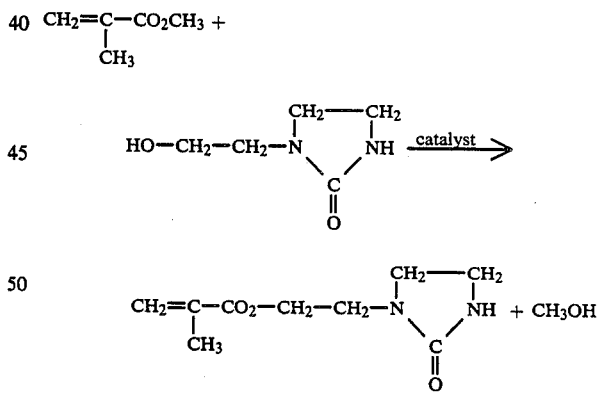

In the process according to the invention it is possible to use an acrylate or methacrylate II where $R^1$ is alkyl of 1 to 4, preferably 1 or 2, carbon atoms. Examples are ethyl, propyl, butyl, i-butyl and in particular methyl methacrylate or acrylate.

A suitable starting material III is any compound where A or B is branched or unbranched alkylene of 2 to 5 carbon atoms, for example $-C_2H_4-$, $-CH(CH_3)CH_2-$, $-CH_2CH(CH_3)-$, $-(CH_2)_3-$, $-(CH_2)_5-$, $-CH_2CH(CH_3)CH_2-$, or $CH_2C(CH_3)_2CH_2-$. Preferably the heterocycle has 5 or 6 ring members. It is particularly advantageous to use 1-(2-hydroxyethyl)imidazolidin-2-one, which is readily obtainable from aminoethylethanolamine and urea, for example as described in U.S. Pat. No. 3,254,075.

A suitable catalyst for the transesterification is according to the invention a titanium alcoholate or chelate of one of the metals of iron, zinc, titanium and/or zirconium with a 1,3-dicarbonyl compound.

In the alcoholate of titanium, the alcohol component can be any alcohol of 1 to 8, in particular 2 to 4, carbon atoms, for example ethanol, propanol, i-propanol, allyl alcohol, n-butanol or i-butanol. The preparation of these compounds is described for example in Houben-Weyl, Methoden der organischen Chemie, 4th edition, volume VI/2, 1963, pages 21–26.

Particularly suitable transesterification catalysts are tetraalkyl titanates, for example tetramethyl, tetrapropyl, tetraisopropyl or tetra-n-butyl titanate.

In the case of the catalysts which are composed of chelates of the abovementioned metals with 1,3-dicarbonly compounds, normally as many molecules of dicarbonyl compound are present as corresponds to the oxidation number of the metal. Suitable chelating agents are 1,3-dicarbonyl compounds such as, for example, ethyl acetoacetate, acetylacetone, 3-methylacetylacetone (3-methylpentane-2,4-dione), benzoylacetone or dibenzylmethane; metal chelates of 1,3-diketones, in particular acetylacetonates, are particularly suitable. The prepartion of metal chelates and their use is described for example in Houben-Weyl, Methoden der organischen Chemie, 4th edition, volume VI/2, 1963, pages 53–55 and 58–61, or A. E. Martell, M. Calvin, Die Chemie der Metallchelatverbindungen (1958).

The catalysts are generally used individually or mixed in amounts of from 0.01 to 10 mol %, based on III. The addition of larger amounts is possible, but is generally not necessary. In the case of acetylacetonates, from 0.05 to 1.0 mol % and in the case of tetra-$C_2$-$C_4$-alkyl titanates from 0.2 to 10 mol % are advantageous.

The ester II can be used in an amount of from 1 to 20, preferably 2 to 10, in particular 3 to 6, moles per mole of III.

The reaction is expediently carried out in the presence of a conventional polymerization inhibitor, for example phenothiazine or hydroquinone monomethyl ether, in particular in the presence of oxygen. The oxygen is generally added in the form of air and in such amounts that the content in the gas phase above the reaction mixture remains below the explosion limit. For example amounts of from 0.1 to 1 l per hour per mole of cyclic urea have proved suitable.

The reaction can be carried out under atmospheric, subatmospheric or superatmospheric pressure. Suitable reaction temperatures range from 30° to 150° C., preferably from 50° to 130° C., in particular from 70° to 120° C. The reaction can be carried out batchwise or continuously. Expediently, the starting materials II and III are brought to the boil together while the alkanol which is eliminated is distilled off continuously, if need be in the form of its azeotrope with ester II. The reaction takes from about 1 to 6 hours, depending on reaction temperature and catalyst. It is possible to carry out the reaction in the presence of an inert solvent, for example toluene or cyclohexane.

On completion of the reaction the catalyst can, if necessary be separated off in a conventional manner. Tetraalkyl titanates can be separated off for example after hydrolysis with water by filtration or centrifugation.

When using zirconium 2,4-pentanedionate it is particularly advantageous, surprisingly, that the separation of a catalyst from the product can be dispensed without impairing the application properties of the product on use in acrylate dispersions.

The product can be isolated from the reaction mixture in a conventional manner, for example by evaporating off excess ester II. However, it is particularly expedient and economical to carry out the reaction with a (meth)acrylate which need not be separated off completely or otherwise for subsequent use in acrylate dispersions, ie. which may be copolymerized.

In the case of conversions of over 90%, the separation of unconverted hydroxy compound III from that product can frequently likewise be dispensed with without loss of quality.

In the preferred range, the product solutions obtained are from 20 to 50% strength and can be directly copolymerized into acrylate dispersions.

EXAMPLE 1

2,700 g of methyl methacrylate were heated to the boil together with 780 g of 1-(2-hydroxyethyl)-imidazolidin-2-one, 13 g of tetraethyl titanate and 2.7 g of phenothiazine while stirring and passing in 0.9 l of air per hour. In the course of 5.3 hours, 212 g of the azetrope of methanol with methyl methacrylate were distilled off at the boiling point of 65° C. through a packed column.

On completion of the reaction, the reaction mixture was cooled down to 25° C., 175 g of water were added to separate off the catalyst, and the resulting precipitate was separated off after 0.5 hours by centrifuging (69 g).

3,387 g were obtained of a solution which, according to quantitative HPLC analysis, contained 31.9% of 1-(2-methacryloyloxyethyl)imidazolidin-2-one, corresponding to a yield of 91%, based on starting 1-(2-hydroxyethyl)imidazolidin-2-one.

EXAMPLE 2

130 g of 1-(2-hydroxyethyl)imidazolidin-2-one, 450 g of methyl methacrylate, 0.7 g of zirconium acetylacetonate and 0.1 g of phenothiazine were heated to the boil while stirring and passing in 0.9 l of air per hour. As in Example 1, 36 g of the azetrope of methanol with methyl methacrylate were distilled off in the course of 2.6 hours.

This left 544 g of product solution which, according to quantitative HPLC analysis, contained 33.4% of 1-(2-methacryloyloxyethyl)imidazolidin-2-one, corresponding to a yield of 91.5% based on starting 1-(2-hydroxyethyl)imidazolidin-2-one. For a 93.7% conversion this corresponds to a selectivity of 97.8%.

EXAMPLE 3

130 g of 1-(2-hydroxyethyl)imidazolidin-2-one, 450 g of methyl methacrylate, 0.7 g of zinc acetylacetonate and 0.1 g of phenothiazine were heated to the boil while stirring and passing in 0.9 l of air per hour. As in Example 1, 40 g of the azeotrope of methanol with methyl methacrylate were distilled off in the course of 3.5 hours.

This left 540 g of product solution which, according to quantitative HPLC analysis, contained 27.7% of 1-(2-methacryloyloxyethyl)imidazolidin-2-one, corresponding to a yield of 75.6% based on starting 1-(2-hydroxyethyl)imidazolidin-2-one. For an 85.5% conversion this corresponds to a selectivity of 88.4%.

EXAMPLE 4

130 g of 1-(2-hydroxyethyl)imidazolidin-2-one, 450 g of methyl methacrylate, 3.5 g of iron acetylacetonate and 0.1 g of phenothiazine were heated to the boil while stirring and passing in 0.9 l of air per hour. As in Example 1, 32 g of azeotrope of methanol with methyl methacrylate were distilled off in the course of 5.3 hours.

This left 550 g of product solution which, according to quantitative HPLC analysis, contained 22.1% 1-(2-methacryloyloxyethyl)imidazolidin-2-one, corresponding to a yield of 61.4% based on starting 1-(2-hydroxyethyl)imidazolidin-2-one. For 68.3% conversion this corresponds to a selectivity of 89.9%.

EXAMPLE 5

1,454.6 g of aminoethylethanolamine and 840 g of urea were heated, after displacement of the supernatant air by nitrogen, to 130° C. in 0.5 hours and then up to 210° C. in the course of 3.5 hours. After further 0.5 hours of heating at 210° C., the ammonia-eliminating reaction was complete.

1,815 g were obtained of a product which, according to qualitative HPLC analysis, contained 96.6% of 1-(2-hydroxyethyl)imidazolidin-2-one, corresponding to a yield of 96.3%

134.9 g of this material were heated to the boil without further purification together with 450 g of methyl methacrylate, 0.49 g of zirconium acetylacetonate and 0.1 g of phenothiazine while stirring and passing in 0.9 l of air per hour. As in Example 1, 37.6 g of the azeotrope of methanol with methyl methacrylate were distilled off in 4.1 hours.

This left 547 g of product solution which, according to quantitative HPLC analysis, contained 33.2% of 1-(2-methacryloyloxyethyl)imidazolidin-2-one, corresponding to a yield of 91.8% based on starting 1-(2-hydroxyethyl)imidazolidin-2-one. For a 93.3% conversion this corresponds to a selectivity of 98.4%.

COMPARATIVE EXPERIMENT 6

130 g of 1-(2-hydroxyethyl)imidazolidin-2-one, 450 g of methyl methacrylate, 1.8 g of 30% strength methanolic sodium methylate solution and 0.1 g of phenothiazine were heated to the boil with stirring. As in Example 1, 38.1 g of the azeotrope of methanol with methyl methacrylate were distilled off in 0.6 hours.

According to analysis by gas chromatography, the reaction mixture contained 1-(2-methacryloyloxy)-3-(2-carbmethoxypropyl)imidazolidin-2-one (byproduct) and 1-(2-methacryloyloxyethyl)imidazolidin-2-one (useful product) in a ratio of 4.3:1.

We claim:

1. A process for preparing an acrylate or methacrylate of the formula I

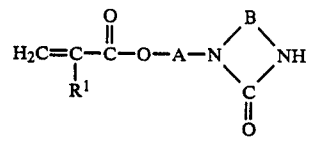

where $R^1$ is hydrogen or methyl and A and B are each branched or unbranched alkylene of 2 to 5 carbon atoms, which comprises reacting an acrylate or methacrylate of the formula II

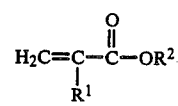

where $R^2$ is alkyl of 1 to 4 carbon atoms with a heterocycle of the formula III

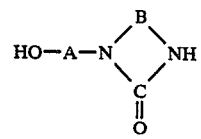

in the presence of a titanium alcoholate or a chelate compound of one of the metals titanium, zirconium, iron or zinc with a 1,3-dicarbonyl compound.

2. The process of claim 1, wherein the reaction is carried out in the presence of a titanium tetraalcoholate.

3. A process as claimed in claim 1, wherein the reaction is carried out in the presence of a acetylacetonate of zirconium, zinc, titanium or iron.

4. A process as claimed in claim 1, wherein methyl or ethyl methacrylate is reacted with 1-(2-hydroxyethyl)imidazolidin-2-one.

5. A process as claimed in claim 1, wherein the alkanol of ester II, which is eliminated in the course of the reaction, is continuously removed from the reaction mixture.

6. A process as claimed in claim 1, wherein the reaction is carried out in the presence of a polymerization inhibitor.

7. A process as claimed in claim 6, wherein the reaction is carried out in the presence of atmospheric oxygen.